(12) United States Patent
Yamaguchi et al.

(10) Patent No.: US 6,750,249 B1
(45) Date of Patent: Jun. 15, 2004

(54) CONTROLLED RELEASE ORAL PREPARATIONS OF ESCULETIN AND ITS DERIVATIVES

(75) Inventors: Iwao Yamaguchi, Saitama (JP); Saichi Ono, Tokyo (JP); Tadahiko Chiba, Tokyo (JP)

(73) Assignee: Kureha Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/806,636

(22) PCT Filed: Oct. 4, 1999

(86) PCT No.: PCT/JP99/05451

§ 371 (c)(1),
(2), (4) Date: May 23, 2001

(87) PCT Pub. No.: WO00/20000

PCT Pub. Date: Apr. 13, 2000

(30) Foreign Application Priority Data

Oct. 6, 1998 (JP) ............................................. 10/299173

(51) Int. Cl.$^7$ .......................... A61K 31/35; A61K 9/16; A61K 9/22; A61K 9/52; A61K 9/62
(52) U.S. Cl. .................. 514/457; 424/400; 424/451; 424/452; 424/457; 424/458; 424/459; 424/461; 424/463; 424/464; 424/465; 424/468; 424/474; 424/475; 424/479; 424/480; 424/489; 424/490; 424/493; 424/494; 424/497
(58) Field of Search .......................... 514/457; 424/400, 424/451, 452, 457, 458, 459, 461, 463, 464, 465, 468, 474, 475, 479, 480, 489, 490, 493, 494, 497

(56) References Cited

U.S. PATENT DOCUMENTS

| | | | |
|---|---|---|---|
| 4,704,285 A | | 11/1987 | Alderman |
| 5,455,268 A | * | 10/1995 | Watanabe et al. |
| 5,574,062 A | * | 11/1996 | Hashimoto et al. |
| 5,681,584 A | * | 10/1997 | Savastano et al. |
| 6,040,434 A | * | 3/2000 | Inaba et al. |

FOREIGN PATENT DOCUMENTS

| | | |
|---|---|---|
| JP | 62-120323 | 6/1987 |
| JP | 4-284022 | 9/1992 |
| JP | 6-9407 | 1/1994 |
| JP | 6-312925 | 11/1994 |
| JP | 10-226641 | 8/1998 |

* cited by examiner

*Primary Examiner*—Gohamudi S. Kishore
*Assistant Examiner*—Simon J. Oh
(74) *Attorney, Agent, or Firm*—Hollander Law Firm, P.L.C.

(57) ABSTRACT

The present invention relates to an oral preparation of esculetin with controlled release. The oral preparation of esculetin with controlled release of the present invention comprises a gel-forming polymer base, preferably hydroxypropylmethylcellulose. The preparation may be coated with an enteric polymer base such as hydroxypropylmethylcellulose acetate succinate to thereby enhance solubility in the intestines.

When orally administered, the preparation can continuously release esculetin. Thus, the administration frequency and dose can be reduced and a therapeutic effect on arthropathy can be established.

30 Claims, No Drawings

CONTROLLED RELEASE ORAL PREPARATIONS OF ESCULETIN AND ITS DERIVATIVES

TECHNICAL FIELD

The present invention relates to a controlled-release oral preparation comprising esculetin or its derivative as an effective component.

Because the controlled-release oral preparation of the present invention can gradually release esculetin or its derivative in a controlled manner over a long period of time, the preparation can maintain the effect of the esculetin or the derivative for a long time by a single administration. As a result, the preparation can improve symptoms such as inflammations, aches, performance disorders, and the like which are induced by a break-down of arthrodial cartilage such as osteoarthropathy, chronic rheumatism, etc.

BACKGROUND ART

Chronic rheumatism, rheumatic fever, osteoarthropathy, and the like are included in the arthropathy. Of these chronic rheumatism and osteoarthropathy are suffered by a great number of patients and thus are considered to be major arthropathy. There are two types of osteoarthropathy; one is congenitus or secondary in nature, and the other is primary and induced by progressive deformation of arthrodial cartilage due to aging. The number of patients suffering from the primary osteoarthropathy has been increasing in recent years as the number of aged people increases. There is a significant difference between the cause of disease and pathology of chronic rheumatism and those of osteoarthropathy. However, these diseases are common inasmuch as the ultimately obstruct joint functions by fracture of the arthrodial cartilage. A primarily chosen medicine for rheumatic diseases such as chronicrheumatism, rheumatic fever, systemic lupus erythematosus, osteoarthropathy, and the like is an analgesicanti-inflammatory agent such as aspirin, indomethacin, or the like. In addition to these medicines, gold preparations such as thiosol, immunomodulating drug, steroid drugs, D-penicillamine, and the like are used as a chronic arthropathy curative medicine. On the other hand, esculetins such as esculetin, 4-methylesculetin and the like are known as medicines possessing a cholesterol reducing effect, vascular reinforcing effect, and anti-oxidation effect (Japanese Patent Publication No. 16626/1967). Carboxylic acid diesters of 4-methyl esculetin having 6–25 carbon atoms, particularly caprylic acid diester lauric acid diester, and palmitic acid diester, are known to exhibit an anti-inflammatory effect (French Patent No. 2276819).

The above conventional analgesic antiinflammation agents not only exhibit no effect of depressing fractures of the arthrodial cartilage, but also some of these agents have been confirmed to have an effect of exacerbating the diseases in an experiment using cartilage cells. Furthermore, no fracture depressant effect of the arthrodial cartilage has been clinically found in the above curative medicines for chronic arthropathy and osteoarthropathy. The arthrodial cartilage consists of cartilage cells and a cartilage matrix. The cartilage matrix has a three-dimensional matrix structure wherein type II collagen which is a cartilage cell-producing fibrous protein and proteoglycan which is a protein polysaccharide composite material, are non-conjunctively bonded and intertwined with hyaluronic acid in a complex manner. The cartilage matrix contains a large quantity of water which contributes to maintaining a normal joint function. The major polysaccharide forming proteoglycan is glycosaminoglycan consisting of chondroitin sulfate and keratan sulfate.

Watanabe et al. found that esculetins such as esculetin, 4-methyl esculetin, and the like strongly depress a decrease in the amount of glycosaminoglycan in the matrix due to stimulation of interleukin-1 and the like, and thus are useful as a protective agent for the arthrodial cartilage. (Japanese Patent Application Laid-open No. 312925/1994).

When orally-administered, these esculetins are immediately metabolized: in the liver and found in blood as a conjugate with glucuronic acid or sulfuric acid. The glucuronic acid conjugate is considered to become esculetin in the arthrodial cartilage and exhibit a cartilage protection effect. However, because the glucuronic acid conjugate has high water solubility and is immediately eliminated from the kidney, there is almost no such substance present in the blood three hours after oral administration. It is necessary for esculetin or a derivative thereof to be continuously present in the cartilage for a long time at a concentration above a certain level (0.01–100, preferably 0.1–10 ng/mg of cartilage) to exhibit the cartilage protection effect, requiring the administration of a large amount of the medicine (200–1,000 mg/kg) several times (6–12 times) a day. Administration of a large amount of the medicine involves a rapid increase in the blood concentration, thereby increasing risks of side effects.

In order to solve these problems, the inventors of the present invention have conducted extensive studies and found that it is possible to continuously maintain the concentration required for the compound to locally exhibit the medical effect (0.01–100, preferably0.1–10ng/mg of cartilage) for a long period of time (10 hours or more) and to reduce side effects at a lower dose than conventional medicines for oral administration by controlling release of esculetin or its derivative from a preparation.

Accordingly, an object of the present invention is to provide a novel arthropathy therapeutic oral preparation comprising esculetin or its derivative which can continuously maintain the local concentration of the effective components by controlled release, even if administered at a small dose, thereby decreasing a risk of side effect.

DISCLOSURE OF THE INVENTION

The present invention has been accomplished to solve these problems and relates to a controlled-release oral preparation such as granules, tablets, capsules, etc. comprising esculetin its derivative, or pharmacologically acceptable salts thereof, which can release the effective components (major medicines esculetin and its derivative) in a controlled manner.

The medicinal effect of esculetin or its derivatives has a correlation with the intracartilaginous concentration of esculetin or its derivatives after administration, esculetin: metabolized from the derivatives, and glucuronic acid conjugates of esculetins which produce esculetin by decomposition with time.

The intracartilaginous concentration of esculetin or its derivatives after administration, esculetin metabolized from the derivatives, and glucuronic acid conjugates of esculetins which produce esculetin by decomposition with time has a correlation with the sum of the blood concentration of esculetin or its derivatives and glucuronic acid conjugates of esculetin or its derivatives. When the sum of: intracartilaginous concentration of esculetin or its derivatives is 0.01 ng/mg of cartilage, the sum of blood concentration of esculetin or its derivatives and 6-position or 7-position glucuronic acid conjugates of esculetin or its derivatives which release esculetin or its derivatives in the cartilage is about 0.5 µmol/L. Therefore, to maintain the medicinal effect of esculetin or its derivatives, the sum of the blood concentration of esculetin or its derivatives and 6-position or 7-position glucuronic acid conjugates of esculetin or its derivatives which release esculetin or its derivatives in the cartilage must be 0.5 µmol/L or more.

Because of the above reasons, there are no limitations to the form and formulation for the oral administration preparation of the present invention inasmuch as the preparation comprises esculetin, its derivatives, or pharmacologicallly acceptable salts thereof as major components, can be orally administered, and, when orally administered to a dog at a dose of 1 to 100 mg/kg, can maintain the blood concentration of 0.5 µmol/L or more of esculetin or its derivatives and 6-position or 7-position glucuronic acid conjugates of esculetin or its derivatives which release esculetin or its derivatives, in the cartilage for a period of 10 hours or more.

BEST MOBE FOR CARRYING OUT THE INVENTION

The esculetin, its derivatives, or the pharmaceutically acceptable salts thereof used as an effective component in the present invention is a compound known in the art and represented by the following formula (I) (Japanese Patent Application Laid-open No. 312925/1994).

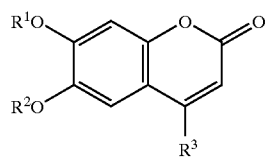

(I)

wherein $R^1$ and $R^2$ are individually a hydrogen atom or a saturated or unsaturated aliphatic acyl group having 2–25 carbon atoms or benzoyl group, and $R^3$ is a hydrogen atom, hydroxyl group, alkyl group, aryl group, or aralkyl group.

Hydrogen atom, acetyl group, pivaloyl group, capryloyl group, lauroyl group, palmitoyl group, stearoyl group, linoleoyl group, docosahexaenoyl group, and benzoyl group are given as preferable examples of the groups $R^1$ and $R^2$ in the formula. (I)

The alkyl group represented by $R^3$ in the above formula (I) is preferably an aliphatic alkyl group, and more preferably a lower alkyl group having 1–4 carbon atoms, such as a methyl group; ethyl group, n-propyl group, isopropyl group, n-butyl group, isobutyl group, s-butyl group, and t-butyl group. Of these, a methyl group and ethyl group are particularly preferable. The aryl group represented by $R^3$ in the above formula (I) is preferably an aryl group having 6–12 carbon atoms such as a phenyl group, naphthyl group, or biphenyl group. One or more hydrogen atoms in these aryl groups may be replaced by a lower alkyl group having 1–4 carbon atoms, halogen atom, or hydroxyl group. The aralkyl group represented by $R^3$ in the above formula (I) is preferably a lower alkyl group having 1–4 carbon atoms substituted by an aryl group having 6–12 carbon atoms such as, for example, a benzyl group, phenylethyl group, phenylpropyl group, and phenylbutyl group. One or more hydrogen atoms on the aryl group of these aralkyl groups may be replaced by, for example, a lower alkyl group having 1–4 carbon atoms, halogen atom, or hydroxyl group.

The pharmaceutically acceptable salt of an esculetin derivative of the present invention is formed with a hydroxyl group at the 6 or 7 position. Salts with an inorganic base or organic base are included in the pharmaceutically acceptable salt. Hydroxides, carbonates, bicarbonates, and the like of ammonium, potassium, sodium, lithium, calcium, magnesium, or aluminum, for example, are given as the inorganic base suitable for forming these salts.

As examples of the organic base, a salt of mono-, di-, or tri-alkylamine such as methylamine, dimethylamine, and triethylamine, salt of mono-, di-, or tri-hydroxyalkylamine, guanidine salt, N-methylglycosamine salt, amino acid salt, and the like can be given.

Esculetin is commercially available and its derivatives can be manufactured by a method described in the above-mentioned laid-open Patent Application.

Preferable esculetin and esculetin derivatives used in the present invention are as:follows: esculetin, 4-methylesculetin, 4-ethylesculetin, 4-(n-propyl)-esculetin, 4-(isopropyl)-esculetin, 4-(n-butyl)-esculetin, 4-(s-butyl)-esculetin, 4-(t-butyl)-esculetin, 4-(isobutyl)-esculetin, 4-methylesculetin 6,7-bis(acetate), 4-methylesculetin 6,7-bis(stearate), 4-methylesculetin 6,7-bis(linolate), 4-methylesculetin 6,7-bis(docosahexaenoate), esculetin 6,7-bis(benzoate), 4-methylesculetin 6,7-bis(benzoate), methyl-esculetin 6,7-bisacetate, esculetin 6,7-bis(pivalate), and esculetin 6-monopivalate.

These compounds induced no deaths or exhibited no conspicuous toxicity when a suspension in a 0.5% methyl cellulose aqueous solution was intraperitoneally administered to Crj: CD-1 (ICR) male mice (age: six weeks, five mice per group) once a day for four consecutive days.

Furthermore, a culture broth obtained by culturing a mixture of cartilage cells aseptically extracted from the articulation genus cartilage of rabbits, a cartilage fracture factor (forbolmyristate acetate), and the above compounds exhibited a remarkable suppression of a decrease in the amount of glycosaminoglycan which constitutes the cartilage matrix, confirming that these compounds have an effect of depressing arthrodial cartilage fracture.

In addition, in an experiment comprising extracting the cartilage from the head of femur of an SD-series male rat, aseptically embedding the extracted cartilage into the shaved back of a BALB/C female mouse, administering the above compounds to the mouse, and measuring proteoglycan constituting the cartilage matrix in the head of femur, it was found that a decrease in the amount of the proteoglycan was suppressed, indicating that these compounds have an effect of depressing arthrodial cartilage fracture.

The period of time required for the oral administration preparation of the present invention comprising esculetin, its derivative, or a pharmaceutically acceptable salt thereof as a main component to dissolve 80% of the main component was between 0.5 and 23 hours, when evaluated by the dissolution test according to the paddle method of the Japanese Pharmacopoeia (paddle rotation: 100 rpm, test solution: purified water, test solution temperature: 37° C.). For the preparation of the present invention to maintain the blood concentration, in terms of the sum of the concentration of esculetin or its derivatives and the concentration of 6-position or 7-position glucuronic acid, conjugates of esculetin or its derivatives which release esculetin or its derivatives in the cartilage, of 0.5 µmol/L or more, when 1 to 100 mg/kg of the preparation is administered to a dog, the period of time required for the preparation to dissolve 80% of the main component as determined according to the above dissolution test method must be 0.5 to 23 hours. Such a preparation is preferably in the form of granules, tablets, or capsules into which the granules are filled.

The amount of esculetin or its derivative in the preparation is usually from 1–99 wt % (hereinafter indicated simply by "%"), preferably from 5–70%, and more preferably from 10 to 40%.

The granules are prepared by mixing esculetin, its derivative, or a pharmaceutically acceptable salt thereof, a base component for controlling release of the active component, an excipient, binder, disintegrator, and the like, and granulating the mixture by a known granulation method. Either the dry granulating method or wet granulation method is applicable.

A method of using a slug machine and a method of using a roller compactor are given as the dry granulating method. A wet screening method, rolling granulation method, and pulverization granulation method are given as examples of the wet granulation method. As required, the release control action of the granules may be adjusted by providing the granules with a coating. The-release control action of the granules may also be adjusted by producing granules by mixing esculetin, its derivative, or a pharmaceutically acceptable salt thereof, and additives commonly used for the preparation of granules such as an excipient, binder, disintegrator, and the like, and coating the granules with an enteric coating base, an insoluble coating base, or the like.

The tablets are prepared by mixing esculetin, its derivative, or a pharmaceutically acceptable salt thereof, a base component for controlling release of the active component, an excipivent, binder, disintegrator, and the like, granulating the mixture by a known granulation method, and tabletting the granules after the addition of a lubricant. The tablets are also prepared by mixing esculetin, its derivative, or a pharmaceutically acceptable salt thereof, a base component for controlling release of the active component, an excipient binder, disintegrator, and the like, then directly tabletting the mixture with the addition of a lubricant.

Either the dry granulating method or wet granulation method is applicable to the preparation of granules for tabletting. A method of using a slug machine and a method of using a roller compactor are given as the dry granulating method. An extrusion granulation method, rolling granulation method, and pulverization granulation method are given as examples of the wet granulation method.

As required, the release control action of the tablets may be adjusted by providing the tablets with a coating. The release control action of the tablets may also be adjusted by producing tablets from esculetin, its derivative, or a pharmaceutically acceptable salt thereof, and additives commonly used for the preparation of tablets, and providing the tablets with a coating of an enteric coating base, an insoluble coating base, or the like.

The capsules are prepared by mixing esculetin, its derivative, or a pharmaceutically acceptable salt thereof, a base component for controlling release of the active component, an excipient, binder, disintegrator, and the like, and granulating the mixture by a known granulation method, and filling the granules into capsules. Any of gelatine capsules, hydroxypropylmethylcellulose capsules, hydroxypropylmethylcellulose acetate succinate capsules may be used for the preparation of the capsules.

As required, the release control action of the capsules may be adjusted by providing the capsules with a coating. The release control action of the capsules may also be adjusted by producing granules from esculetin, its derivative, or a pharmaceutically acceptable salt thereof, and additives commonly used for the preparation of granules, filling the granules into capsules, and providing the capsules with a coating of an enteric coating base, an insoluble coating base, or the like.

The base material used for the release control is preferably a gel-forming polymer base.

As the gel-forming polymer base, carmellose sodium, methylcellulose, hydroxyethylcellulose, hydroxypropylcellulose, and hydroxypropylmethylcellulose are preferable. Of these, hydroxypropylmethylcellulosel is particularly preferable. As hydroxypropylmethylcellulose, hydroxypropylmethylcellulose 2910, hydroxypropylmethylcellulose 2208, and hydroxypropylmethylcellulose 2906 are preferable.

Although the amount of the gel-forming polymer base to be added varies according to the properties and amount of esculetin, its derivative, or the pharmacologically acceptable salt, the properties and molecular weight of the gel-forming polymer base, the types and amount of other additives, and the type of the preparation, the addition in the amount of 0.5–90%, preferably 10–70%, and more preferably 35–70% can ensure that the resulting preparation elutes 80% of esculetin or its derivative in a period of 0.5 to 23 hours, thereby enabling the preparation to maintain the target blood concentration.

Known excipients, binders, disintegrators, and lubricants can be used for the preparation. Crystalline cellulose/starch, lactose, and the like can be given as examples of vehicles. As examples of binders, hydroxypropylcellulose, polyvinyl alcohol, polyvinyl pyrrolidone, and the like can be given. As examples of disintegrators, low-substituted hydroxypropylcellulose, croscarmellose sodium, crospovidone, and the like can be given. As lubricants, talc, magnesium stearate, and the like can be given. Other additives such as a coloring agent, perfume, stabilizer, preservative, taste improver, antioxidant, and the like may be added as required.

When controlling release of the active component from granules by coating or to provide the preparation with a release control effect, an enteric coating base or an insoluble coating base is preferably used.

Hydroxypropylmethylcellulose acetate succinate, hydroxypropylmethylcellulose phthalate, cellulose acetate phthalate, carboxymethylethylcellulose, methacrylic acid copolymer L, and methacrylic acid copolymer S are preferably used as the enteric coating base. Of these, hydroxypropylmethylcellulose acetate succinate and hydroxypropylmethylcellulose phthalate are particularly preferable.

As the insoluble coating base, ethyl cellulose and aminoalkylmethacrylate copolymer RS are preferable, with the former being more preferred.

A known coating apparatus can be used for the enteric coating or insoluble coating. A fluidized bed granulator, a centrifugal granulation coating apparatus, and the like can be given.

Although the amount of the enteric coating base (coating ratio) varies according to the form and formulation of the preparation, the type, properties, and molecular weight of the coating base, the period of time for which dissolution is controlled, and the like, about 0.5–50%, and preferably about 1–20% of the total weight of the preparation is used.

The insoluble coating operation is performed using a mixture of an insoluble coating base and a suitable water-soluble coating base. Hydroxypropylmethylcellulose 2910 is given as an example of the water-soluble coating base. Although the ratio of the insoluble coating base and water-soluble coating base varies according to the form and formulation of the preparation; and the type, properties, and molecular weight of the coating base, the period of time for which dissolution is controlled, and the like, the ratio of about 1:10 to 10:1, and preferably about 3:7 to 7:3, is applied. The coating ratio is about 0.5 to 50%, and preferably about 1–20 of the weight of the granules.

It is particularly preferable that the preparation of the present invention comprises 0.5 to 90% of a gel-forming polymer base and 0.5 to 50% of an enteric coating base and/or an insoluble coating base.

The present invention will be described in more detail by way of examples.

However, these examples should not be construed as limiting the present invention.

EXAMPLE 1

<Tablets Containing Hydroxypropylmethylcellulose Having the Following Formulation>

| Raw materials | Amount |
| --- | --- |
| Esculetin | 50 mg |
| Low-substituted hydroxypropylcellulose | 30 mg |
| Hydroxypropylcellulose | 30 mg |
| Hydroxypropylmethylcellulose 2910* | 143 mg |
| Lactose | 143 mg |
| Magnesium stearate | 4 mg |

*Metlose 60SH-50 (a product of Shin-Etsu Chemical Co., Ltd., the indicated viscosity: 50 cSt, substituted methoxy group: 28.0 to 30.0%, hydroxypropoxyl group: 7.0 to 12.0%) was used as hydroxypropylmethylcellulose 2910.

Tablets were prepared by mixing raw materials other than magnesium stearate, kneading the mixture with purified water in the amount of 35% by weight of the mixture, granulating the kneaded product from a wet screener, adding magnesium stearate to the dried granules, and tabletting the dry mixture.

EXAMPLE 2

<Tablets Containing Hydroxypropylmethylcellulose Having the Following Formulation>

| Raw materials | Amount |
| --- | --- |
| Esculetin | 50 mg |
| Low-substituted hydroxypropylcellulose | 30 mg |
| Hydroxypropylcellulose | 30 mg |
| Hydroxypropylmethylcellulose 2910* | 143 mg |
| Lactose | 143 mg |
| Magnesium stearate | 4 mg |

*Metlose 60SH-4000 (a product of Shin-Etsu Chemical Co., Ltd., the indicated viscosity: 4000 cSt, substituted methoxy group: 28.0 to 30.0%, hydroxypropoxyl group: 7.0 to 12.0%) was used as hydroxypropylmethylcellulose 2910.

Tablets were prepared by mixing raw materials other than magnesium stearate, kneading the mixture with purified water in the amount of 35% by weight of the mixture, granulating the kneaded product from a wet screener, adding magnesium stearate to the dried granules, and tabletting the dry mixture.

EXAMPLE 3

<Tablets Containing Hydroxypropylmethylcellulose Having the Following Formulation>

| Raw materials | Amount |
| --- | --- |
| Esculetin | 50 mg |
| Low-substituted hydroxypropylcellulose | 30 mg |
| Hydroxypropylcellulose | 30 mg |
| Hydroxypropylmethylcellulose 2910* | 143 mg |
| Lactose | 143 mg |
| Magnesium stearate | 4 mg |

*TC-5E (a product of Shin-Etsu Chemical Co., Ltd., the indicated viscosity: 3 cSt, substituted methoxy group: 28.0 to 30.0%, hydroxypropoxyl group: 7.0 to 12.0%) was used as hydroxypropylmethylcellulose 2910.

Tablets were prepared by mixing raw materials other than magnesium stearate, kneading the mixture with purified water in the amount of 35% by weight of the mixture, granulating the kneaded product from a wet screener, adding magnesium stearate to the dried granules, and tabletting the dry mixture.

EXAMPLE 4

<Tablets Containing Hydroxypropylmethylcellulose Having the Following Formulation>

| Raw materials | Amount |
| --- | --- |
| Esculetin | 150 mg |
| Low-substituted hydroxypropylcellulose | 30 mg |
| Hydroxypropylcellulose | 30 mg |
| Hydroxypropylmethylcellulose 2910* | 143 mg |
| Lactose | 43 mg |
| Magnesium stearate | 4 mg |

*Metlose 60SH-50 was used as hydroxypropylmethylcellulose 2910.

The tablets were prepared by weighing and mixing all raw materials, and directly subjecting the mixture to the powder compression method.

EXAMPLE 5

<Enteric Capsule Preparation with the Esculetin-containing Granules Having the Following Formulation Filled in Hydroxypropylmethylcellulose Acetate Succinate (HPMC-AS) Capsules>

| Raw materials | Amount (wt %) |
| --- | --- |
| Esculetin | 75% |
| Low-substituted hydroxypropylcellulose | 15% |
| Hydroxypropylcellulose | 5% |
| Sodium Croscarboxymethylcellulose | 4% |
| Magnesium stearate | 1% |

Granules were prepared by a dry granulation method using a roller compactor. The granules were filled into #1 hydroxypropylmethylcellulose acetate succinate capsules in an amount of 200 mg/capsule to prepare a capsule preparation.

EXAMPLE 6

<Enteric Capsule Preparation with the Esculetin-containing Granules Having the Following Formulation Filled in HPMC-AS: Capsules>

| Raw materials | Amount (wt %) |
| --- | --- |
| Esculetin | 37.5% |
| Low-substituted hydroxypropylcellulose | 7.5% |
| Hydroxypropylcellulose | 7.5% |
| Hydroxypropylmethylcellulose (Metlose 60SH-4000) | 17.875% |
| Hydroxypropylmethylcellulose (TC-5E) | 17.875% |
| Lactose | 10.75% |
| Magnesium stearate | 1% |

Tablets prepared from the raw materials with above formulation by the wet granulation compression method were pulverized and sieved to collect granules with a size from 500 to 1400 µm. The granules were filled into #0 hydroxypropylmethylcellulose acetate succinate capsules in the amount of 267 mg/capsule.

EXAMPLE 7
<Enteric Capsule Preparation with the Esculetin-containing Granules Having the Following Formulation Filled in HPMC-AS Capsules>

| Raw materials | Amount (wt %) |
| --- | --- |
| Esculetin | 37.5% |
| Low-substituted hydroxypropylcellulose | 7.5% |
| Hydroxypropylcellulose | 7.5% |
| Hydroxypropylmethylcellulose (Meltose 60SH-4000) | 35.75% |
| Lactose | 10.75% |
| Magnesium stearate | 1% |

Tablets prepared from the raw materials with the above formulation by the wet granulation compression method were pulverized and sieved to collect granules with a size from 500 to 1400 µm. The granules were filled into #0 hydroxypropylmethylcellulose acetate succinate capsules in the amount of 267 mg/capsule.

EXAMPLE 8
<Enteric Capsule Preparation with the Esculetin-containing Granules Having the Following Formulation Filled in Hydroxypropylmethylcellulose Acetate Succinate Capsules>

| Raw materials | Amount (wt %) |
| --- | --- |
| Esculetin | 37.5% |
| Low-substituted hydroxypropylcellulose | 7.5% |
| Hydroxypropylcellulose | 7.5% |
| Hydroxypropylmethylcellulose (Metlose 60SH-4000) | 30% |
| Lactose | 16.5% |
| Magnesium stearate | 1% |

Granules were prepared by mixing raw materials other than magnesium stearate, kneading the mixture with purified water in the amount of 35% by weight of the mixture, granulating the kneaded product from a wet screener, and adding magnesium stearate to the dried granules. The granules were filled into #1 hydroxypropylmethylcellulose acetate guccinate capsules in an amount of 200 mg/capsule to prepare a capsule preparation.

EXAMPLE 9
<Capsules Prepared from Granules Containing Esculetin and Other Components of Following Formulation by Coating the Surface of the Granules with a 4:6 Mixture of Ethylcellulose and Hydroxypropylmethylcellulose 2910 (TC-5R) at a Granule/Coating Ratio of 90:10, then Filling the Granules into Gelatin Capsules>

| Raw materials | Amount (wt %) |
| --- | --- |
| Esculetin | 23.33% |
| Corn starch | 30.40% |
| Sucrose starch sphere | 44.30% |
| Hydroxypropylcellulose | 0.98% |
| Magnesium stearate | 1.00% |

Granules were prepared by combining white sucrose starch sphere with a mixture of esculetin and corn starch using an aqueous solution of hydroxypropylcellulose as a binder by a centrifugal granulator. Granules were coated by spraying a solution of ethylcellulose and hydroxypropylmethylcellulose 2910 (TC-5R) in a methylene chloride/acetone mixture with a suitable plasticizer added thereto.

EXAMPLE 10
<Enteric Tablet Preparation Prepared by Coating the Tablets Having the Following Formulation with Hydroxypropylmethylcellulose Acetate Succinate to a Tablet/Coating Ratio of 90:10 by Weight>

| Raw materials | Amount |
| --- | --- |
| Esculetin | 150 mg |
| Low-substituted hydroxypropylcellulose | 30 mg |
| Hydroxypropylcellulose | 30 mg |
| Hydroxypropylmethylcellulose (TC-5E) | 143 mg |
| Lactose | 43 mg |
| Magnesium stearate | 4 mg |

Tables were prepared by a wet granule compression method and coated by spraying a solution of hydroxypropylmethylcellulose acetate succinate in a methylene chloride/acetone mixture with a suitable plasticizer added thereto.

EXAMPLE 11
<Enteric Tablet Preparation Prepared by Coating the Tablets Having the Following Formulation with Hydroxypropylmethylcellulose Acetate Succinate to a Tablet/Coating Ratio of 90:10 by Weight>

| Raw materials | Amount |
| --- | --- |
| Esculetin | 150 mg |
| Low-substituted hydroxypropylcellulose | 30 mg |
| Hydroxypropylcellulose | 30 mg |
| Hydroxypropylmethylcellulose (TC-5S) | 143 mg |
| Lactose | 43 mg |
| Magnesium stearate | 4 mg |

Hydroxyprbpylmethylcellulose (TC-5S). (a product of Shin-Etsu Chemical Co., Ltd.) has an indicated viscosity of 15 cSt, a substituted methoxy group content of 28.0 to 30.0%, and a hydroxypropoxyl group content of 7.0 to 12.0%.

Tablets were prepared by a wet granule compression method and coated by spraying a solution of hydroxypropylmethylcellulose acetate succinate in a methylene chloride/acetone mixture with a suitable plasticizer added thereto.

EXAMPLE 12
<Capsules Prepared from Granules Containing Esculetin Having the Following Formulation by Coating the Surface of the Granules with a Methacrylic Acid Copolymer S at a Granule/Coating Ratio of 90:10 by Weight, then Filling the Granules into Gelatin Capsules>

| Raw materials | Amount (wt %) |
|---|---|
| Esculetin | 23.33% |
| Corn starch | 30.40% |
| Sucrose starch sphere | 44.30% |
| Hydroxypropylcellulose | 0.98% |
| Magnesium stearate | 1.00% |

Granules were prepared by combining sucrose starch sphere with a mixture of esculetin and corn starch using an aqueous solution of hydroxypropylcellulose as a binder by a centrifugal granulator. Granules were coated by spraying a solution of methacrylic acid copolymer S in a methylene chloride/acetone mixture with a suitable plasticizer added thereto.

Control Example 1

Tablets containing hydroxypropylmethylcellulose having 1.0 the following formulation

| Raw materials | Amount |
|---|---|
| Esculetin | 50 mg |
| Low-substituted hydroxypropylcellulose | 30 mg |
| Hydroxypropylcellulose | 30 mg |
| Hydroxypropylmethylcellulose 2910* | 286 mg |
| Magnesium stearate | 4 mg |

*Metlose 60SH-50 was used as hydroxypropylmethylcellulose 2910

Tablets were prepared by mixing raw materials other than magnesium stearate, kneading the mixture with purified water in the amount of 75% by weight of the mixture, granulating the kneaded product from a wet screener, adding magnesium stearate to the dried granules, and tabletting the dry mixture.

Control Example 2

Fast release esculetin tablets prepared using the following formulation

| Raw materials | Amount |
|---|---|
| Esculetin | 50 mg |
| Low-substituted hydroxypropylcellulose | 30 mg |
| Hydroxypropylcellulose | 30 mg |
| Lactose | 286 mg |
| Magnesium stearate | 4 mg |

Tablets were prepared by mixing raw materials other than magnesium stearate, kneading the mixture with purified water in the amount of 15% by weight of the mixture, granulating the kneaded product from a wet screener, adding magnesium stearate to the dried granules, and tabletting the dry mixture.

Experimental Example 1

Dissolution tests performed under the following conditions using the preparations obtained in Examples 1–12 and Control Examples 1–2 confirmed that the period of time required for the preparations of Examples 1–12 to dissolve 80% of esculetin was between 0.5 and 23 hours, whereas the corresponding time was 4.8 hours for the preparation of Control Example 1 and 0.2 5 hour for the preparation of Control Example 2.

(Dissolution Test Conditions)
Test method: Paddle method (100 rpm)
Temperature: 37±1° C.
Test solution amount: 900 mL Purified water (pH 6.0), Liquid II of Japanese Pharmacopoeia (pH 6.8, herein called "Liquid II"), or a buffer solution (pH 7.5) were used as a test solution.

<Table>
The period of time required for the preparations of Examples 1–12 and Control Examples 1–2 to elute 80% of esculetin

|  | Test solution | Hour* |
|---|---|---|
| Example 1 | Purified water | 5 |
| Example 2 | Purified water | 20 |
| Example 3 | Purified water | 2 |
| Example 4 | Purified water | 12 |
| Example 5 | Liquid II | 0.5 |
| Example 6 | Liquid II | 2 |
| Example 7 | Liquid II | 4 |
| Example 8 | Liquid II | 8 |
| Example 9 | Purified water | 3 |
| Example 10 | Liquid II | 2 |
| Example 11 | Liquid II | 4 |
| Example 12 | pH 7.5 Buffer solution | 0.5 |
| Control Example 1 | Purified water | 48 |
| Control Example 2 | Purified water | 0.25 |

*The period of time required for 80% of esculetin to be eluted

Experimental Example 2

The preparations obtained in Examples 1–12 and Control Examples 1–2 were orally administered to beagle dogs at a dose of 30 mg/kg of esculetin to measure the concentration of glucuronic acid conjugates of esculetin in plasma 0.5, 1, 2, 4, 6, 8, 10, 12, and 24 hours after the administration. It was confirmed that the concentration of 0.5 $\mu$mol/L or more was maintained for 10 hours or more using the preparations of Examples 1–12, whereas that concentration was maintained for only 1.5 hours using the preparations of Control Examples 1–2.

<Table>
The period of time for which the concentration of glucuronic acid conjugates of 0.5 $\mu$mol/L or more was maintained after administration of the preparations of Examples 1–12 and Control Examples 1–2 to beagle dogs

|  | The period of time for which the concentration was maintained 0.5 $\mu$mol/L or more (After administration) | Duration for which the concentration was maintained 0.5 $\mu$mol/L or more |
|---|---|---|
| Example 1 | After 0.5–12 hours | 11.5 hours |
| Example 2 | After 2–12 hours | 10 hours |
| Example 3 | After 0.5–24 hours | 23.5 hours |
| Example 4 | After 0.5–24 hours | 23.5 hours |
| Example 5 | After 0.5–12 hours | 11.5 hours |
| Example 6 | After 2–24 hours | 22 hours |
| Example 7 | After 2–24 hours | 22 hours |
| Example 8 | After 0.5–24 hours | 23.5 hours |

| | The period of time for which the concentration was maintained 0.5 µmol/L or more (After administration) | Duration for which the concentration was maintained 0.5 µmol/L or more |
|---|---|---|
| Example 9 | After 0.5–24 hours | 23.5 hours |
| Example 10 | After 0.5–24 hours | 23.5 hours |
| Example 11 | After 0.5–24 hours | 23.5 hours |
| Example 12 | After 0.5–12 hours | 11.5 hours |
| Control Example 1 | After 0.5–2 hours | 1.5 hours |
| Control Example 2 | After 0.5–2 hours | 1.5 hours |

Industrial Applicability

The present invention provides a novel arthropathy therapeutic oral preparation comprising esculetin or its derivative which can continuously maintain the local concentration of the effective components by controlled release, even if administered at a small dose, thereby decreasing a risk of side effect.

Oral administration of the controlled-release preparation of esculetin or its derivative of the present invention ensures that the concentration of glucuronic acid conjugates in blood is maintained at 0.5 µmol/L or more for a long period of time (10 hours or more) to exhibit a cartilage protection effect, thereby reducing a dose as well as decreasing frequency of administration to 1–2 times a day.

What is claimed is:

1. A controlled-release oral preparation comprising:
   a granulated mixture of: a) esculetin, or its derivative shown by the formula (I),

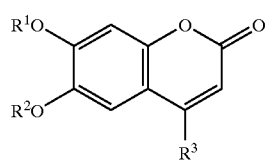

wherein $R^1$ and $R^2$ are individually a hydrogen atom or a saturated or unsaturated aliphatic acyl group having 2–25 carbon atoms or a benzoyl group, and $R^3$ is a hydrogen atom, hydroxyl group, alkyl group, aryl group, or aralkyl group, or a pharmaceutically acceptable salt thereof as an effective component; and b) a gelforming polymer base; and
   an enteric capsule containing the granulated miture.

2. The controlled-release oral preparation of esculetin according to claim 1, wherein the enteric capsule comprises an enteric coating base selected from the group consistng of hydroxypropylmethylcellulose acetate succinate, hydroxypropylmethylcellulose phthalate, cellulose acetate phthalate, carboxymethylethylcellulose, and methacrylic acid copolymer.

3. The controlled-release oral preparation of esculetin according to claim 1, containing 0.5 to 90 wt % of the gel-forming polymer base.

4. The controlled-release oral preparation of esculetin according to claim 2, wherein the gel-forming polymer base is hydroxypropylmethylcellulose.

5. The controlled-release oral preparation of esculetin according to claim 1, containing 0.5 to 50 wt % of an insoluble coating base.

6. The controlled-release oral preparation of esculetin according to claim 5, wherein the insoluble coating base is ethylcellulose.

7. The controlled-release oral preparation of esculetin according to claim 1, wherein the release of esculetin or its derivative is controlled so that the concentration of glucuronic acid conjugates in plasma is maintained at 0.5 µmol/L or more for a period of 10 hours or more after administration when the preparation is orally administered to a beagle dog at a dose of 1–100 mg/kg.

8. The controlled-release oral preparation of esculetin according to claim 1, wherein the release of esculetin is controlled so that the period of time required for the preparation to dissolve 80 wt % of esculetin is 0.5 to 23 hours as determined by the dissolution test according to the paddle method of the Japanese Pharmacopoeia.

9. The contolled-release oral preparation of esculetin according to claim 3, wherein the release of esculetin or its derivative is controlled so that the concentration of glucuonic acid conjugates in plasma is maintained at 0.5 µmol/L or more for a period of 10 hours or more after administration when the preparation is orally administered to a beagle dog at a dose of 1–100 mg/kg.

10. The controlled-release oral preparation of esculetin according to claim 4, wherein the release of esculetin or its derivative is controlled so that the concentration of glucuronic acid conjugates in plasma is maintained at 0.5 µmol/L or more for a period of 10 hours or more after administration when the preparation is orally administered to a beagle dog at a dose of 1–100 mg/kg.

11. The controlled-release oral preparation of esculetin according to claim 5, wherein the release of esculetin or its derivative is controlled so that the concentration of glucuronic acid conjugates in plasma is maintained at 0.5 µmol/L or more for a period of 10 hours or more after administration when the preparation is orally administered to a beagle dog at a dose of 1–100 mg/kg.

12. The controlled-release oral preparation of esculetin according to claim 6, wherein the release of esculetin or its derivative is controlled so that the concentration of glucuronic acid conjugates in plasma is maintained at 0.5 µmol/L or more for a period of 10 hours or more after administration when the preparation is orally administered to a beagle dog at a dose of 1–100 mg/kg.

13. The controlled-release oral preparation of esculetin according to claim 3, wherein the release of esculetin is controlled so that the period of time required for the preparation to dissolve 80 wt % of esculetin is 0.5 to 23 hours as determined by the dissolution test according to the paddle method of the Japanese Phamacopoeia.

14. The controlled-release oral preparation of esculetin according to claim 4, wherein the release of esculetin is controlled so that the period of time required for the preparation to dissolve 80 wt % of esculetin is 0.5 to 23 hours as determined by the dissolution test according to the paddle method of the Japanese Pharmacopoeia.

15. The controlled-release oral preparation of esculetin according to claim 5, wherein the release of esculetin is controlled so that the period of time required for the preparation to dissolve 80 wt % of esculetin is 0.5 to 23 hours as determined by the dissolution test according to the paddle method of the Japanese Pharmacopoeia.

16. The controlled-release oral preparation of esculetin according to claim 6, wherein the release of esculetin is controlled so that the period of time required for the preparation to dissolve 80 wt % of esculetin is 0.5 to 23 hours as determined by the dissolution test according to the paddle method of the Japanese Pharmacopoeia.

17. The controlled-release oral preparation according to claim 5, wherein the insoluble coating base is an aminoalkylmethacrylate copolymer.

18. A controlled-release oral preparation consisting essentially of:
   a tablet consisting essentially of a compressed mixture of:
   a) esculetin, or its derivative shown by formula (I),

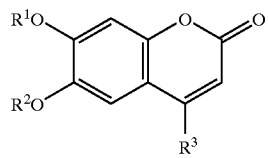

wherein $R^1$ and $R^2$ are individually a hydrogen atom or a saturated or unsaturated aliphatic acyl group having 2–25 carbon atoms or a benzoyl group, and $R^3$ is a hydrogen atom, hydroxyl group, alkyl group, aryl group, or aralkyl group, or a pharmaceutically acceptable salt thereof as an effective component; and b) a gel-forming polymer base; and
   an enteric coating base on the compressed mixture.

19. The controlled-release oral preparation of esculetin according to claim 18, wherein the enteric coating base is selected from the group consisting of hydroxypropylmethylcellulose acetate succinate, hydroxypropylmethylcellulose phthalate, cellulose acetate phthalate, carboxymethylethylcellulose, and methacrylic acid copolymer.

20. The controlled-release oral preparation of esculetin according to claim 18, containig 0.5 to 50 wt % of the enteric coating base.

21. The controlled-release oral preparation of esculetin according to claim 20, wherein the enteric coating base is selected from the group consisting of hydroxypropylmethylcellulose acetate succinate, hydroxyproplmethylcellulose phthalate, cellulose acetate phthalate, carxboymethylethylcellulose, and methacrylic acid copolymer.

22. The controlled-release oral preparation of esculetin according to 20, wherein the release of esculetin or its derivative is controlled so that the concentration of glucuronic acid conjugates in plasma is maintained at 0.5 μmol/L or more for a period of 10 hours or more after administraion when the preparation is orally administered to a beagle dog at a dose of 1–100 mg/kg.

23. The controlled-release oral preparation of esculetin according to claim 21, wherein the release of esculetin or its derivative is controlled so that the concentration of glucuronic acid conjugates in plasma is maintained at 0.5 μmol/L or more for a period of 10 hours or more after administration when the preparation is orally administered to a beagle dog at a dose of 1–100 mg/kg.

24. The controlled-release oral preparation of esculetin according to claim 20, wherein the release of esculetin is controlled so that the period of time required for the preparation to dissolve 80 wt % of esculetin is 0.5 to 23hours as determined by the dissolution test according to the paddle method of the Japanese Pharmacopoeia.

25. The controlled-release oral preparation of esculetin according to claim 21, wherein the release of esculetin is controlled so that the period of time required for the preparation to dissolve 80 wt % of esculetin is 0.5 to 23 hours as detemined by the dissolution test according to the paddle method of the Japanese Pharmacopoeia.

26. A controlled-release oral preparation consisting essentially of:
   a tablet consisting essetially of a compressed mixture of:
   a) esculetin, or its derivative shown by the fornula (I),

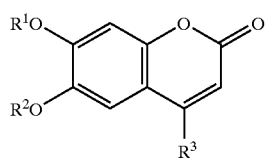

wherein $R^1$ and $R^2$ are individually a hydrogen atom or a saturated or unsaturated aliphatic acyl group having 2–25 carbon atoms or a benzoyl group, and $R^3$ is a hydrogen atom, hydroxyl group, alkyl group, aryl group, or aralkyl group, or a pharmaceutically acceptable salt thereof as an effective component; and b) a gel-forming polmer base; and
   an enteric coating base on the compressed mixture; and
   an insoluble coating base.

27. The controlled-release oral preparation of esculetin according to claim 26, comprising 0.5 to 90 wt % of the gel-forming polymer base, and 0.5 to 50 wt % of the enteric coating base and 0.5 to 50 wt % of the insoluble coating base.

28. The controlled-release oral preparation of esculetin according to claim 27, wherein the release of esculetin or its derivative is controlled so that the concentration of glucuronic acid conjugates in plasma is maintained at 0.5 μmol/L or more for a period of 10 hours or more after administration when the preparation is orally admninistered to a beagle dog at a dose of 1–100 mg/kg.

29. The controlled-release oral preparation of esculetin according to claim 27, wherein the release of esculetin is controlled so that the period of time required for the preparation to dissolve 80 wt % of esculetin is 0.5 to 23 hour as determined by the dissolution test according to the paddle method of the Japanese Pharmacopoeia.

30. The controlled-release oral preparation of esculetin according to claim 27, wherein the enteric coating base is selected from the group consistng of hydroxypropylmethylcellulose acetate succinate, hydroxypropylmethylcellulose phthalate, cellulse acetate phthalate, carboxymethylethylcellulose, and methacrylic acid copolymer, and the insoluble coating base is selected frm the group consisting of ethylcellulose and aminoalkylmethacrylate copolymer.

* * * * *